United States Patent
Hayashi et al.

(10) Patent No.: US 6,919,481 B1
(45) Date of Patent: Jul. 19, 2005

(54) ALKOXYAMINES CONTAINING A VINYL GROUP, THEIR APPLICATIONS AND METHODS OF THEIR PRODUCTION

(75) Inventors: Masaki Hayashi, Aichi (JP); Tomoyuki Nakamura, Aichi (JP); Norihisa Ujikawa, Aichi (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 09/959,754

(22) PCT Filed: May 17, 2000

(86) PCT No.: PCT/JP00/03170

§ 371 (c)(1),
(2), (4) Date: Nov. 6, 2001

(87) PCT Pub. No.: WO00/78709

PCT Pub. Date: Dec. 28, 2000

(30) Foreign Application Priority Data

| Jul. 22, 1998 | (JP) | 10-206146 |
| Jun. 23, 1999 | (JP) | 11/177422 |
| Aug. 27, 1999 | (JP) | 11/242052 |

(51) Int. Cl.$^7$ .................................. C07C 259/00
(52) U.S. Cl. ........................ 564/300; 564/1; 514/315
(58) Field of Search ................... 514/315; 564/300, 564/1

(56) References Cited

U.S. PATENT DOCUMENTS

| 6,107,425 A | * 8/2000 | Sinta et al. | 526/313 |
| 6,258,905 B1 | * 7/2001 | Wu et al. | 526/217 |
| 6,632,895 B1 | * 10/2003 | Melchiors et al. | 526/90 |

FOREIGN PATENT DOCUMENTS

| JP | 5-6537 | 1/1993 |
| JP | 5-59070 | 3/1993 |
| JP | 10-60064 | 3/1998 |
| JP | 11-171946 | 6/1999 |
| JP | 2000-95744 | 4/2000 |

OTHER PUBLICATIONS

C. Hawker et al., "Preparation of Hyperbranched and Star Polymers by a 'Living', Self–Condensing Free Radical Polymerization", J. Am. Chem. Soc., vol. 117, No. 43, pp. 10763–10764, 1995.

* cited by examiner

Primary Examiner—Tatyana Zalukaeva
(74) Attorney, Agent, or Firm—Wenderoth, Lind & Ponack, L.L.P.

(57) ABSTRACT

Alkoxyamines containing a vinyl group as represented by the following general formula (1) are produced in a method which comprises a process of heating divinyl benzene, nitroxide compound and organic peroxide up to a temperature at which the organic peroxide decomposes thermally:

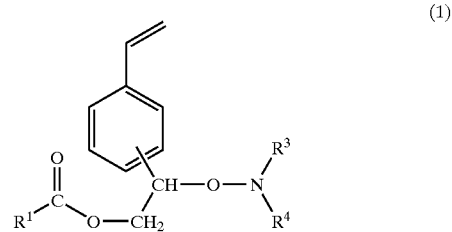

(1)

(In the formula, $R^1$ represents an aryl group or an $R^2O$ group, wherein $R^2$ represents a linear or branched alkyl group having 1–12 carbon atoms or a cycloalkyl group. $R^3$ and $R^4$ are each tertiary alkyl group having 4–6 carbon atoms or of cyclic structure where $R^3$ and $R^4$ are connected with each other having a total carbon number of 8–16. In case of cyclic structure, they are optionally substituted either by an alkyl group, an oxo group, a hydroxyl group, an acyloxy group or an alkoxy group.) Furthermore, graft polymers can be produced by the use of high molecular radical polymerization initiators from which an alkoxyamine group suspends.

5 Claims, 1 Drawing Sheet

ALKOXYAMINES CONTAINING A VINYL GROUP, THEIR APPLICATIONS AND METHODS OF THEIR PRODUCTION

This application is a 371 of PCT/JP00/03170 filed May 17, 2000.

TECHNICAL FIELD

This invention relates to new alkoxyamines containing a vinyl group in their molecules and the methods for producing them, and to high molecular radical polymerization initiators with an alkoxyamine group of specific structure suspending from their molecular main chain of high polymer of radical-polymerizing monomers and the methods for producing them, as well as to graft polymers obtainable by means of such high molecular radical polymerization initiators.

TECHNICAL BACKGROUND

Alkoxyamines containing a vinyl group in their molecules are known. Processes for producing such alkoxyamines are disclosed, for example, in the laid-open patent Tokukai-Sho 60-89452 and Angew. Chem. Int. Ed. Engl., 34, 1456–1459 (1995).

Namely, the alkoxyamine containing a vinyl group described in the laid-open patent Tokukai-Sho 60-89452 is obtainable by synthesis of alkoxyamine containing an OH group using special compound of azo system having an OH group in its molecule, followed by esterification of the alkoxyamine through reaction of its OH group with (meth) acryloyl chloride.

On the other hand, in the process described in Angew. Chem. Int. Ed. Engl., 34, 1456–1459 (1995), benzoyl peroxide is pyrolyzed in styrene solution under the existence of nitroxide compound. After the product of pyrolysis has hydrolyzed to produce alkoxyamine having an OH group in its molecule, alkoxyamine containing a vinyl group is obtained by introducing a vinyl group into the alkoxyamine having an OH group through reaction with chloromethylstyrene.

In the case of the said alkoxyamines containing a vinyl group according to the disclosed conventional processes, however, alkoxyamines with a functional group including an OH group are first synthesized and then combined with other vinyl compounds through ionic reaction such as esterification, etc., so that they are sensitive to ionic reaction at the combined point and thus show disadvantage to easily be dissociated to return to alkoxyamines without any vinyl group.

Moreover, all of the said conventional processes are very complicated and not desirable from industrial viewpoints because they need at least 2 steps reaction for obtaining alkoxyamines containing a vinyl group.

One of the purposes of this invention is, therefore, to provide new alkoxyamines containing a vinyl group whose frameworks are stable against ionic reaction and are useful at the same time as free radical generator, etc., as well as to provide a simple method for producing them.

On the other hand, processes for obtaining graft polymers by radical polymerization are known and disclosed, for example, in the laid-open patents Tokukai-Sho 60-89452, Tokukai-Hei 10-60064 and Tokukai-Hei 11-171946, Angew. Chem. Int. Ed. Engl., 34, 1456 (1995), Angew. Chem. Int. Ed. Engl., 36, 270 (1997) and Macromolecules, 31, 4396 (1998), which use high molecular radical polymerization initiators containing an alkoxyamine group in their molecules under the influences of stable free radicals.

The processes for obtaining high molecular radical polymerization initiators containing an alkoxyamine group in their molecules can roughly be classified into two types. In one type of process, compounds of high molecular weight have been synthesized in advance of introductions of an alkoxyamine group into their molecules through radical reaction or ionic reaction to obtain high molecular radical polymerization initiators (in the following called "Method I"). In case of the other type of process, monomer compounds containing both a radical-polymerizing vinyl group and an alkoxyamine group within the same molecule (in the following called "alkoxyamine containing a vinyl group") are synthesized first, and then, the monomer compounds are copolymerized with other monomers to increase their molecular weight to form high molecular radical polymerization initiators (in the following called "Method II").

In conventional processes, graft polymers are synthesized from high molecular radical polymerization initiators which have been obtained in one of the said two methods.

In case of the laid-open patents Tokukai-Sho 60-89452, Tokukai-Hei 10-60064 and Tokukai-Hei 11-171946 as well as Angew. Chem. Int. Ed. Engl., 36, 270 (1997), high molecular radical polymerization initiators are obtained by the said "Method I".

According to the process described in the laid-open patent Tokukai-Sho 60-89452, a high polymer with general structure (polybutadien or poly(isobutyl methacrylate)) is synthesized first. Radicals generated in the said high polymer by abstraction of a hydrogen atom under the existence of nitroxide are then allowed to react with nitroxide existing in the system so as to produce high molecular radical polymerization initiator containing an alkoxyamine group suspending in its molecule.

According to the process described in the laid-open patent Tokukai-Hei 10-60064, radicals generated by photo radiation in high polymer molecule is allowed to react with nitroxide existing in the system so as to produce high molecular radical polymerization initiator containing an alkoxyamine group in its molecule.

In case of the process described in the laid-open patent Tokukai-Hei 11-171946, a peroxide group is introduced into high polymer by ozonization of polyethylene or by copolymerization of monomers containing a peroxide group in their molecules with other monomers. Then, radicals arising out of the said peroxide group by thermal cracking are allowed to react with monomers and nitroxide existing in the system in order to produce high molecular radical polymerization initiator containing an alkoxyamine group in its molecule.

According to Angew. Chem. Int. Ed. Engl., 36, 270 (1997), high molecular radical polymerization initiator containing an alkoxyamine group suspending in the high polymer molecule is obtained by producing high polymer containing a benzyl chloride group by copolymerization of styrene and chloromethyl styrene, followed by reaction of the benzyl chloride group with alkoxyamine having an OH group in its molecule.

On the other hand, high molecular radical polymerization initiators are obtained by the said "Method II" in case of the laid-open patent Tokukai-Sho 60-89452, Angew. Chem. Int. Ed. Engl., 34, 1456 (1995) and Macromolecules, 31, 4396 (1998).

Namely, according to the laid-open patent Tokukai-Sho 60-89452, radicals mainly of carbon arising out of azo compound with an OH group by pyrolysis are allowed to react with nitroxide to produce alkoxyamine with an OH group. Then, alkoxyamine containing a vinyl group is obtained by esterification of this OH group with (meth) acryloyl chloride and is further copolymerized with other monomers in order to produce radical polymerization initiator in the form of oligomer (compound of a relatively low molecular weight of 5,000 or less).

Angew. Chem. Int. Ed. Engl., 34, 1456 (1995) describes a process in which alkoxyamine containing a vinyl group, which has been obtained by reaction of chloromethyl styrene with alkoxyamine having an OH group in advance, is copolymerized with styrene so as to produce high molecular radical polymerization initiator having main chain of styrene.

Macromolecules, 31, 4396 (1998) describes a process in which alkoxyamine containing a non-conjugate vinyl group, which has been obtained by reaction between a compound with a non-conjugate vinyl group and alkoxyamine with an OH group, is copolymerized with propylene or 2-methylpentene by means of a metallocene catalyzer.

Alkoxyamine with an OH group mentioned in Angew. Chem. Int. Ed. Engl., 34, 1456 (1995) and Macromolecules, 31, 4396 (1998) is obtained by hydrolysis of the product of pyrolysis of benzoyl peroxide under the existence of nitroxide compound and styrene monomers.

The high molecular radical polymerization initiators obtained by the said conventional processes as well as the graft polymers synthesized by use of them have shown, however, the following problems:

The processes classified into "Method I" in which high molecular radical polymerization initiators are obtained through reactions of high polymer compounds as the starting material, such as hydrogen abstraction from high polymer according to the laid-open patent Tokukai-Sho 60-89452, photo reaction of high molecular compound according to the laid-open patent Tokukai-Hei 10-60064, cracking of a peroxide group in high polymer according to the laid-open patent Tokukai-Hei 11-171946, reaction of active site in high polymer according to Angew. Chem. Int. Ed. Engl., 36, 270 (1997), etc. have been unpractical because the high polymers used for those reactions have to satisfy specific requirements, respectively; they must have a hydrogen atom allowing selective and easy abstraction, they must be capable of generating radicals through light radiation or thermal treatment, they must have active site capable of reacting with an OH group, etc.

Besides, in the above mentioned processes, excessive quantities of nitroxide over the radicals arising on high molecular compounds must exist within the systems for the purpose of effective introduction of nitroxide into the high molecular compounds, what causes disadvantages in cost and requires additional processes for removing surplus nitroxide which have not participated in reactions from the produced high molecular radical polymerization initiators. Furthermore, these processes are unpractical also from industrial points of view since reactions are not easy because high polymers are used as starting materials, special equipment such as light radiator, etc. is needed, the use of solvents is inevitable and so on.

As for the process to obtain high molecular radical polymerization initiators, "Method II", is superior to "Method I" at the above mentioned points, but still has been combined with the following problems:

In the process described in the laid-open patent Tokukai-Sho 60-89452, oligomeric radical polymerization initiator and further graft oligomer are obtained by use of alkoxyamine containing a vinyl group synthesized by esterification reaction. It shows, therefore, a structure of trunk and branch polymer combined with each other by ester bond. Since ester bond is naturally sensitive to ionic reaction, an alkoxyl group is easily released from oligomeric radical polymerization initiator. Even when graft polymer is once obtained, the branch polymer is eliminated easily so that it cannot exhibit its properties as graft polymer. It is expected from this structural defect that a coating by this graft polymer may be inferior in water resistance, resistance against acid rain, weatherproofness, etc.

The invention described in the laid-open patent Tokukai-Sho 60-89452 aims specially at obtaining oligomer so that it provides only graft polymer of a relatively low molecular weight, especially as to the branch polymer, and that the characteristics of branch polymer cannot sufficiently be exhibited. The graft polymer concerned has, therefore, been combined with the problem that it does not show sufficient effects when it is used as compatibilizer, emulsifying agent, separation stabilizing agent, etc. for mixtures consisting of 2 or more types of high polymers.

Similarly, the process described in Angew. Chem. Int. Ed. Engl., 34, 1456 (1995) provides graft polymer which has a benzilic hydrogen bonding to an oxygen atom, which is very active to radical reaction, at the combined point of trunk and branch polymer. Thus, this graft polymer has a latent structural defect that it deteriorates through decomposition as a result of gradual abstraction of such a benzilic hydrogen by oxygen radicals in the air, for example, and has a high potential of release of branch polymer from trunk. Furthermore, as for graft polymer obtainable by means of the high molecular radical polymerization initiator, synthesis of graft copolymer composed of 2 or more types of monomers is not described concretely besides description about reaction for obtaining branched styrene homopolymer. Branched homopolystyrene indicates no effects as compatibilizer, emulsifing agent, separation stabilizing agent, etc.

As being a compound with a non-conjugate vinyl group derived from aliphatic end olefin compound, the alkoxyamine containing a vinyl group described in Macromolecules, 31, 4396 (1998) allows only limited types of monomers to be copolymerized with each other if attempting to obtain high molecular radical polymerization initiator by means of radical copolymerization executable easily on industrial basis. In other words, it is difficult to obtain high molecular radical polymerization initiator with high polymer main chain composed of (meth)acrylic derivative monomers or monomers with a conjugate vinyl group such as styrene, etc.

In addition, all processes described in Angew. Chem. Int. Ed. Engl., 34, 1456 (1995) and Macromolecules, 31, 4396 (1998) require at least 3 steps reaction for obtaining alkoxyamine containing a vinyl group for the purpose of synthesis of high molecular radical polymerization initiator to be very disadvantageous in view of cost and not practical.

In consideration of the above mentioned state of things, it is the additional purposes of this invention to provide a simple process for obtaining high molecular radical polymerization initiators, which are useful in production of graft polymers, and have an alkoxyamine group bonding to their molecular main chain by carbon-to-carbon bond, as well as to provide the high molecular radical polymerization initiators obtained in such process. It is another purpose of this invention to provide high purity graft polymers stable against ionic reaction and radical reaction free from formation of homopolymers of monomers which essentially composing the branch polymer, by means of the said high molecular radical polymerization initiators.

DISCLOSURE OF THE INVENTION

After examining intensively the problems of the said conventional processes seeking for solution, the inventors found that new alkoxyamines containing a vinyl group can be obtained in a simple process comprising a single step by means of industrially available, cheap raw materials and completed this invention.

Namely, the first object of this invention is to provide alkoxyamines containing a vinyl group as represented by the following general formula (1):

(1)

(In the formula, $R^1$ represents an aryl group or an $R^2O$ group, wherein $R^2$ represents a linear or branched alkyl group having 1–12 carbon atoms or a cycloalkyl group. $R^3$ and $R^4$ are each tertiary alkyl group having 4–6 carbon atoms or of cyclic structure where $R^3$ and $R^4$ connected with each other having a total carbon number of 8–16. In case of cyclic structure, they are optionally substituted either by an alkyl group, an oxo group, a hydroxyl group, an acyloxy group or an alkoxy group.)

The said alkoxyamines containing a vinyl group can be produced by heating a mixture comprising divinyl benzene, nitroxide compound and organic peroxide up to the thermal decomposition temperature of the organic peroxide. The organic peroxide should preferably be aromatic diacyl peroxide or peroxydicarbonate.

The inventors found further that alkoxyamines containing a vinyl group with an OH group as represented by the following formula (2) are obtainable from the said stable alkoxyamines containing a vinyl group by substituting their specific portions with an OH group, and that they are useful for enabling introduction of a functional group or as ring-opening polymerization initiator.

(2)

(In the formula, $R^3$ and $R^4$ are each tertiary alkyl group having 4–6 carbon atoms or of cyclic structure where $R^3$ and $R^4$ are connected with each other having a total carbon number of 8–16. In case of cyclic structure, they are optionally substituted either by an alkyl group, an oxo group, a hydroxyl group, an acyloxy group or an alkoxy group.)

Incidentally, the alkoxyamines containing a vinyl group as represented by the said general formula (2) can be produced by hydrolysis of the alkoxyamines containing a vinyl group as represented by the said general formula (1).

Additionally, the inventors found that high molecular radical polymerization initiators are obtainable by use of specific alkoxyamines containing a vinyl group obtained in a simple process comprising a single step by means of industrially available cheap raw materials. The inventors also found that high purity graft polymers showing extremely low homopolymer contents can be obtained by polymerization using the said high molecular radical polymerization initiators. The trunk and branch polymers of the graft polymers are combined with each other by stable carbon-to-carbon bond due to the bonding between molecular main chain and an alkoxyamine group of the high molecular radical polymerization initiators. Furthermore, the each branch polymer of the said graft polymer is of a uniform molecular weight and a narrow polydispersity.

Namely, another aspect of this invention relates to high molecular radical polymerization initiators in the form of high polymer obtained by polymerization of radical-polymerizing monomers, from the main chain of which an alkoxyamine group as represented by the following formula (3) suspends:

(3)

(In the formula, $R^5$ represents an unsubstituted phenylene group or a phenylene group having a substituted group on the ring, $R^6$ represents a hydrogen, a tertiary alkyl group having 4–8 carbon atoms, a benzoyl group, a methylbenzoyl group or an $R^{13}OC(O)$ group, where $R^{13}$ represents a linear or branched alkyl group or an alkoxy alkyl group having 1–10 carbon atoms or an unsubstituted cycloalkyl group having a substituted group on the ring. $R^7$–$R^{12}$ are each linear or branched alkyl group having 1–10 carbon atoms selected independently, or of cyclic structure where $R^7$ and $R^{10}$ are connected with each other having a total carbon number of 4–10. In case of cyclic structure, they are optionally substituted either by an alkyl group, a hydroxy group, an acetoxyl group, a benzoyloxy group, a methoxy group or an oxo group.)

Still another aspect of the invention relates to the process for producing high molecular radical polymerization initiators characterized in that a mixture comprising compound (A) having both a radical-polymerizing vinyl group and an alkoxyamine group within the same molecule as represented by the following general formula (4), radical polymerizing monomers (B1) and radical polymerization initiator (C) is heated in a temperature range where the said radical polymerization initiator (C) decomposes whereas the said compound (A) does not decompose:

(4)

(In the formula, $R^5$ represents an unsubstituted phenylene group or a phenylene group having a substituted group on the ring, $R^6$ represents a hydrogen, a tertiary alkyl group having 4–8 carbon atoms, a benzoyl group, a methylbenzoyl group or an $R^{13}OC(O)$ group, where $R^{13}$ represents a linear or branched alkyl group or an alkoxy alkyl group having 1–10 carbon atoms or an unsubstituted cycloalkyl group having a substituted group on the ring. $R^7$–$R^{12}$ are each linear or branched alkyl group having 1–10 carbon atoms selected independently, or of cyclic structure where $R^7$ and $R^{10}$ are connected with each other having a total carbon number of 4–10. In case of cyclic structure, they are optionally substituted either by an alkyl group, a hydroxy group, an acetoxyl group, a benzoyloxy group, a methoxy group or an oxo group. $R^{14}$ represents a hydrogen or a methyl group.)

Further aspect of this invention relates to graft polymers obtained by heating high molecular radical polymerization initiators with a suspending alkoxyamine group as represented by the said general formula (3) and radical-polymerizing monomers (B2) in a temperature range between 100° C. and 180° C.

BEST MODE FOR CARRYING OUT THE INVENTION

The mode for carrying out this invention as to alkoxyamine containing a vinyl group is described first in detail.

Alkoxyamine containing a vinyl group in accordance with this invention is a compound as represented by the said general formula (1). In the general formula (1), $R^1$ represents an aryl group or an $R^2O$ group, wherein $R^2$ represents a linear or branched alkyl group having carbon atoms between 1 and 12, preferably 3 and 10, or a cycloalkyl group.

$R^3$ and $R^4$ are each tertiary alkyl group of a carbon number between 4 and 6, or of cyclic structure where $R^3$ and $R^4$ are connected with each other having a total carbon number of between 8 and 16, preferably between 8 and 12. In case of cyclic structure, they are optionally substituted either by an alkyl group, an oxo group, a hydroxyl group, an acyloxy group or an alkoxy group.

Concrete compounds of alkoxyamine containing a vinyl group representable by the general formula (1) according to this invention are, for example, 2-(benzoyloxy)-1-(2',2',6',6'-tetramethyl-1'-piperidinyloxy)-1-(4'-vinylphenyl)ethane,
2-(4'-methylbenzoyloxy)-1-(2',2',6',6'-tetramethyl-1'-piperidinyloxy)-1-(4'-vinylphenyl)ethane,
2-(isopropyloxycarbonyloxy)-1-(2',2',6',6'-tetramethyl-1'-piperidinyloxy)-1-(4'-vinylphenyl)ethane,
2-(isopropyloxycarbonyloxy)-1-(2',2',6',6'-tetramethyl-1'-piperidinyloxy)-1-(3'-vinylphenyl)ethane,
2-(n-propyloxycarbonyloxy)-1-(2',2',6',6'-tetramethyl-1'-piperidinyloxy)-1-(4'-vinylphenyl)ethane,
2-(2'-ethoxyethyloxycarbonyloxy)-1-(2',2',6',6'-tetramethyl-1'-piperidinyloxy)-1-(4'-vinylphenyl)ethane,
2-(3'-methoxybutyloxycarbonyloxy)-1-(2',2',6',6'-tetramethyl-1'-piperidinyloxy)-1-(4'-vinylphenyl)ethane,
2-(cyclohexyloxylcarbonyloxy)-1-(2',2',6',6'-tetramethyl-1'-piperidinyloxy)-1-(4'-vinylphenyl)ethane,
2-(2'-ethylhexyloxycarbonyloxy)-1-(2',2',6',6'-tetramethyl-1'-piperidinyloxy)-1-(4'-vinylphenyl)ethane,
2-(4'-t-butylcyclohexyloxycarbonyloxy)-1-(2',2',6',6'-tetramethyl-1'-piperidinyloxy)-1-(4'-vinylphenyl)ethane,
2-(isopropyloxycarbonyloxy)-1-(4'-benzoyloxy)-2',2',6',6'-tetramethyl-1'-piperidinyloxy)-1-(4'-vinylphenyl)ethane,
2-(isopropyloxycarbonyloxy)-1-(4'-acetoxy-2',2',6',6'-tetramethyl-1'-piperidinyloxy)-1-(4'-vinylphenyl)ethane,
2-(isopropyloxycarbonyloxy)-1-(4'-hydroxy-2',2',6',6'-tetramethyl-1'-piperidinyloxy)-1-(4'-vinylphenyl)ethane,
2-(isopropyloxycarbonyloxy)-1-(2'2'5'5'-tetramethyl-1'-pyrrolidinyloxy)-1-(4'-vinylphenyl)ethane,
2-(isopropyloxycarbonyloxy)-1-(di-t-butylnitroxyl)-1-(4'-vinylphenyl)ethane, etc.

The alkoxyamine containing a vinyl group represented by the general formula (1) according to this invention can be produced by heating a mixture comprising divinylbenzene, nitroxide compound and organic peroxide where oxy-radicals are generated. In the mixture, these oxy-radicals react with the divinylbenzene to generate carbon-centered radicals which are then captured by the nitroxide compound.

Concretely, the said nitroxide compound can be, for example, 2,2,6,6-tetramethylpiperidine-1-oxyl, 4-oxo-2,2,6,6-tetramethylpiperidine-1-oxyl, 4-hydroxy-2,2,6,6-tetramethylpiperidine-1-oxyl, 4-methoxy-tetramethylpiperidine-1-oxyl, 4-benzoyloxy-2,2,6,6-tetramethylpiperidine-1-oxyl, 4-acetoxy-2,2,6,6-tetramethylpiperidine-1-oxyl, 2,2,5,5-tetramethylpyrrolidine-1-oxyl, 1,1,3,3-tetramethylisoindolyne-2-oxyl, di-t-buthylnitroxide, etc.

The said organic peroxide is not limited to any special types.

For example, alkylhydroperoxide, dialkylperoxide, diacylperoxide, peroxydicarbonate, acylsulfonylperoxide, peroxyester, peroxycarbonate, ketoneperoxide, peroxyketal, etc. can be used. Among them, those organic peroxides are especially preferable which decompose thermally and generate oxy-radicals selectively. Besides, for avoiding decomposition of alkoxyamine, those organic peroxides should be preferred which decompose at a temperature under 120° C. For these reasons, aromatic diacylperoxide and peroxydicarbonate are most preferable.

Concretely, benzoyl peroxide, 4,4'-dimethylbenzoylperoxide, di-isopropylperoxydicarbonate, di-n-propylperoxydicarbonate, di-2-ethoxyethylperoxydicarbonate, di-3-methoxybutylperoxydicarbonate, dicyclohexylperoxydicarbonate, di-2-ethylhexylperoxydicarbonate, bis-(4-t-butylcyclohexyl) peroxydicarbonate, etc. can be named as organic peroxide.

The method of decomposition of these organic peroxides is not limited; they may decompose thermally or optically or by reduction-oxidation under the existence of promoter, etc.

The mixing ratio of nitroxide compound to peroxide (nitroxide compound/peroxide) used for obtaining the alkoxyamine containing a vinyl group as represented by the general formula (1) in accordance with this invention should preferably be between 0.3 and 4.0 (molar ratio), but more preferably between 0.6 and 2.0. A ratio under 0.3 is not preferable because carbon centered radicals cannot be captured sufficiently by nitroxide compound and polymers are generated. A ratio over 4.0 is also not preferable because of the economic disadvantage due to lower yield for nitroxide compound.

Divinylbenzene used for obtaining the alkoxyamine containing a vinyl group represented by the general formula (1) according to this invention may be either meta compound (1,3-divinyl benzene), para compound (1,4-divinyl benzene) or mixture of meta and para compounds.

The ratio of divinylbenzene to nitroxide compound (divinylbenzene/nitroxide compound) used in this invention should preferably be between 1 and 100 (molar ratio), but more preferably between 3 and 20. A ratio under 1 makes it difficult to introduce alkoxyamine into only one of vinyl groups of divinylbenzene and thus tends to generate bifunctional alkoxyamine. On the other hand, a ratio over 100 tends to leave a quantity of unreacted divinylbenzene.

The reaction temperature at synthesizing the alkoxyamine containing a vinyl group in accordance with this invention should preferably be between 10° C. and 120° C., but more preferably between 40° C. and 100° C. A temperature under 10° C. is disadvantageous because peroxides decompose slower, while a temperature over 120° C. tends to cause decomposition or polymerization of generated alkoxyamine containing a vinyl group.

The alkoxyamine containing a vinyl group having an OH group in accordance with this invention is a compound represented by the general formula (2). In the general formula (2), $R^3$ and $R^4$ are each tertiary alkyl group having 4–6 carbon atoms or of cyclic structure where $R^3$ and $R^4$ connected with each other having a total carbon number of 8–16. In case of cyclic structure, they are optionally substituted either by an alkyl group, an oxo group, a hydroxyl group, an acyloxy group or an alkoxy group.

The following can be named concretely as the compound of alkoxyamine containing a vinyl group having an OH group in accordance with this invention:

2-hydroxy-1-(2',2',6',6'-tetramethyl-1'-piperidinyloxy)-1-(4'-vinylphenyl)ethane,
2-hydroxy-1-(2',2',6',6'-tetramethyl-1'-piperidinyloxy)-1-(3'-vinylphenyl)ethane,
2-hydroxy-1-(4'-hydroxy-2',2',6',6'-tetramethyl-1'-piperidinyloxy)-1-(4'-vinylphenyl)ethane,
2-hydroxy-1-(4'-benzoyloxy-2',2',6',6'-tetramethyl-1'-piperidinyloxy)-1-(4'-vinylphenyl)ethane,
2-hydroxy-1-(2',2',5',5'-tetramethyl-1'-pyrrolidinyloxy)-1-(4'-vinylphenyl)ethane,
2-hydroxy-1-(di-t-butylnitroxyl)-1-(4'-vinylphenyl)ethane, etc.

The alkoxyamine containing a vinyl group having an OH group represented by the general formula (2) according to this invention can be produced by hydrolysis of the ester bond (a carbonyldioxy group) portion of alkoxyamine containing a vinyl group represented by the said general formula (1).

The aforesaid hydrolysis of the ester bond (a carbonyldioxy group) is not limited to any specific methods, but may be performed in usual methods, for example, by heating after addition of alkali such as sodium hydroxide, etc.

This invention is described in detail in the following on the basis of some working examples, to which the working of the invention is, however, not limited.

EXAMPLE 1

Synthesis of 2-benzoyloxy-1-(2',2',6',6'-tetramethyl-1'-piperidinyloxy)-1-(4'-vinylphenyl)ethane 1.56 g (10 mmol) of 2,2,6,6-tetramethylpiperidine-1-oxyl was dissolved in 15.0 g of 1,4-divinylbenzene. After being added with 1.86 g (7.69 mmol) benzoyl peroxide, the solution was heated for 3.5 hours at 95° C. in nitrogen gas flow.

The solution was then concentrated under reduced pressure and 1.72 g of objective substance was obtained by column chromatography (on silica gel; solution of dichloromethane/n-hexane (1/1) mixture as eluting solution), which corresponded to a yield of 42.3%.

For identifying this substance, $^1$H nuclear magnetic resonance ($^1$H-NMR) analysis, mass spectrum (MS) analysis and element analysis were performed to have the results as given below.

It was confirmed from these analytical results that the obtained substance was 2-(benzoyloxy)-1-(2',2',6',6'-tetramethyl-1'-piperidinyloxy)-1-(4'-vinylphenyl)ethane having a structure as represented by the following formula (5):

(5)

$^1$H-NMR (ppm, dichloroform (CDCl$_3$)/tetramethylsilane (TMS)): 0.70–1.52 (18H), 4.54 (1H), 4.84 (1H), 5.01 (1H), 5.25 (1H), 5.76 (1H), 6.74 (1H), 7.25–7.95 (9H)

MS (FAB, m/e): 408 [M+H]$^+$

Element analysis (as C, H, N)

|  | C | H | N |
|---|---|---|---|
| Measured value (%) | 76.64 | 8.14 | 3.47 |
| Calculated value (%) | 76.63 | 8.16 | 3.44 |

EXAMPLE 2

Synthesis of 2-isopropyloxycarbonyloxy)-1-(2',2',6',6'-tetramethyl-1'-piperidinyloxy)-1-(4'-vinylphenyl)ethane 1.56 g (10 mmol) of 2,2,6,6-tetramethylpiperidine-1-oxyl was dissolved in 15.0 g of 1,4-divinylbenzene and cooled down to 0° C.

After being added with 2.08 g (10 mmol) of di-isopropyloxydicarbonate, the solution was heated for 5 hours at 55° C. in nitrogen gas flow.

The solution was then concentrated under reduced pressure and 2.96 g of objective substance was obtained by column chromatography (on silica gel; solution of dichloromethane/n-hexane (1/1) mixture as eluting solution), which corresponded to a yield of 76.1%. For identifying this substance, $^1$H-NMR analysis, $^{13}$C nuclear magnetic resonance ($^{13}$C-NMR) analysis, MS analysis and element analysis were performed to have the results as given below. It was confirmed from these analytical results that the obtained substance was 2-(isopropyloxycarbonyloxy)-1-(2', 2',6',6'-tetramethyl-1'-piperidinyloxy)-1-(4'-vinylphenyl) ethane having a structure as represented by the following formula (6):

(6)

¹H-NMR (ppm, CDCl₃/TMS):
0.70–1.50 (24H), 4.31 (1H), 4.64 (1H), 4.76 (1H), 4.92 (1H), 5.22 (1H), 5.74 (1H), 6.70 (1H), 7.25–7.40 (4H)

¹³C-NMR (ppm, CDCl₃/TMS):
16.97, 20.15, 21.54, 33.80, 34.09, 40.26, 59.91, 68.74, 71.67, 83.44, 113.48, 125.78, 127.78, 136.49, 136.78, 139.70, 154.38

MS (FAB, m/e): 390 [M+H]⁺

Element analysis (as C, H, N)

|  | C | H | N |
| --- | --- | --- | --- |
| Measured value (%) | 70.90 | 9.02 | 3.55 |
| Calculated value (%) | 70.92 | 9.06 | 3.60 |

EXAMPLE 3

Synthesis of 2-isopropyloxycarbonyloxy)-1-(2',2',6', 6'-tetramethyl-1'-piperidinyloxy)-1-(3'-vinylphenyl) ethane By reaction in accordance with Example 2 except for the use of 1,3-divinylbenzene instead of 1,4-divinylbenzene, 2.74 g of objective substance was obtained, which corresponded to a yield of 70.5%.

For identifying this substance, ¹H-NMR analysis, ¹³C-NMR analysis, MS analysis and element analysis were performed to have the results as given below. It was confirmed from these analytical results that the obtained substance was 2-(isopropyloxycarbonyloxy)-1-(2',2',6',6'-tetramethyl-1'-piperidinyloxy)-1-(3'-vinylphenyl)ethane having a structure as represented by the following formula (7):

(7)

¹H-NMR (ppm, CDCl₃/TMS):
0.70–1.50 (24H), 4.31 (1H), 4.65 (1H), 4.76 (1H), 4.93 (1H), 5.24 (1H), 5.75 (1H), 6.72 (1H), 7.20–7.40 (4H)

¹³C-NMR (ppm, CDCl₃/TMS):
16.96, 20.15, 21.50, 33.78, 34.07, 40.26, 59.88, 68.74, 71.64, 83.61, 113.62, 125.29, 125.58, 127.08, 128.08, 136.74, 137.09, 140.33, 154.35

MS (FAB, m/e): 390 [M+H]⁺

Element analysis (as C, H, N)

|  | C | H | N |
| --- | --- | --- | --- |
| Measured value (%) | 70.91 | 9.03 | 3.56 |
| Calculated value (%) | 70.92 | 9.06 | 3.60 |

EXAMPLE 4

Synthesis of a mixture of 2-(isopropyloxycarbonyloxy)-1-(2',2',6',6'-tetramethyl-1'-piperidinyloxy)-1-(4'-vinylphenyl)ethane and 2-(isopropyloxycarbonyloxy)-1-(2',2',6',6'-tetramethyl-1'-piperidinyloxy)-1-(3'-vinylphenyl)ethane By reaction in accordance with Example 2 except for the use of mixture of 1,3-divinylbenzene and 1,4-divinylbenzene (product of Nippon Steel Chemical Co., Ltd.; trade name: DVB-960) instead of 1,4-divinylbenzene, 2.77 g of objective substance was obtained, which corresponded to a yield of 71.3%.

Judging from the results of ¹H-NMR analysis, ¹³C-NMR analysis, MS analysis and element analysis for identifying this substance, it was confirmed that the obtained substance was the mixture of 2-(isopropyloxycarbonyloxy)-1-(2',2',6',6'-tetramethyl-1'-piperidinyloxy)-1-(4'-vinylphenyl)ethane and 2-(isopropyloxycarbonyloxy)-1-(2',2',6',6'-tetramethyl-1'-piperidinyloxy)-1-(3'-vinylphenyl)ethane.

EXAMPLE 5

Synthesis of 2-(n-propyloxycarbonyloxy)-1-(2',2',6', 6'-tetramethyl-1'-piperidinyloxy)-1-(4'-vinylphenyl) ethane 1.56 g (10 mmol) of 2,2,6,6-tetramethylpiperidine-1-oxyl was dissolved into 15.0 g of 1,4-divinylbenzene and cooled down to 0° C.

After being added with 2.08 g (10 mmol) of di-n-propylperoxydicarbonate, the solution was heated for 5 hours at 55° C. in nitrogen gas flow.

The solution was then concentrated under reduced pressure and 2.90 g of objective substance was obtained by column chromatography (on silica gel; solution of dichloromethane/n-hexane (1/1) mixture as eluting solution), which corresponded to a yield of 74.4%. For identifying this substance, ¹-NMR analysis, ¹³C-NMR analysis, MS analysis and element analysis were performed to have the results as given below. It was confirmed from these analytical results that the obtained substance was 2-(n-propyloxycarbonyloxy)-1-(2',2',6',6'-tetramethyl-1'-piperidinyloxy)-1-(4'-vinylphenyl)ethane having a structure as represented by the following formula (8):

(8)

¹H-NMR (ppm, CDCl₃/TMS):

0.70–1.50 (23H), 3.95 (2H), 4.31 (1H), 4.65 (1H), 4.93 (1H), 5.22 (1H), 5.73 (1H), 6.72 (1H), 7.22–7.40 (4H)

MS (FAB, m/e): 390 [M+H]⁺

Element analysis (as C, H, N)

|  | C | H | N |
|---|---|---|---|
| Measured value (%) | 70.89 | 9.07 | 3.58 |
| Calculated value (%) | 70.92 | 9.06 | 3.60 |

EXAMPLE 6

Synthesis of 2-(2-ethylhexyloxycarbonyloxy)-1-(2',2',6',6'-tetramethyl-1'-piperidinyloxy)-1-(4'-vinylphenyl)ethane

1.56 g (10 mmol) of 2,2,6,6-tetramethylpiperidine-1-oxyl was dissolved into 15.0 g of 1,4-divinylbenzene and cooled down to 0° C.

After being added with 3.85 g (10 mmol) of di-(2-ethylhexyl)-peroxydicarbonate, the solution was heated for 5 hours at 55° C. in nitrogen gas flow.

The solution was then concentrated under reduced pressure and 3.20 g of objective substance was obtained by column chromatography (on silica gel; solution of dichloromethane/n-hexane (1/1) mixture as eluting solution), which corresponded to a yield of 69.6%.

For identifying this substance, ¹H-NMR analysis, MS analysis and element analysis were performed to have the results as given below. It was confirmed from these analytical results that the obtained substance was 2-(2-ethylhexyloxycarbonyloxy)-1-(2',2',6',6'-tetramethyl-1'-piperidinyloxy)-1-(4'-vinylphenyl)ethane having a structure as represented by the following formula (9):

(9)

¹H-NMR (ppm, CDCl₃/TMS):

0.70–1.72 (33H), 3.90 (2H), 4.30 (1H), 4.65 (1H), 4.92 (1H), 5.21 (1H), 5.72 (1H), 6.71 (1H), 7.22–7.39 (4H)

MS (FAB, m/e): 460 [M+H]⁺

Element analysis (as C, H, N)

|  | C | H | N |
|---|---|---|---|
| Measured value (%) | 73.12 | 9.88 | 3.02 |
| Calculated value (%) | 73.16 | 9.87 | 3.05 |

EXAMPLE 7

Synthesis of 2-(4'-t-butylcyclohexyloxycarbonyloxy)-1-(2',2',6',6'-tetramethyl-1'-piperidinyloxy)-1-(4'-vinylphenyl)ethane 1.56 g (10 mmol) of 2,2,6,6-tetramethylpiperidine-1-oxyl was dissolved into 15.0 g of 1,4-divinylbenzene and cooled down to 0° C.

After being added with 4.20 g (10 mmol) of bis-(4-t-butylcyclohexyl)-peroxydicarbonate, the solution was heated for 5 hours at 57° C. in nitrogen gas flow.

The solution was then concentrated under reduced pressure and 3.46 g of objective substance was obtained by column chromatography (on silica gel; solution of dichloromethane/n-hexane (1/1) mixture as eluting solution), which corresponded to a yield of 71.4%. For identifying this substance, ¹H-NMR analysis, MS analysis and element analysis were performed to have the results as given below. It was confirmed from these analytical results that the obtained substance was 2-(4'-t-butylcyclohexyloxycarbonyloxy)-1-(2',2',6',6'-tetramethyl-1'-piperidinyloxy)-1-(4'-vinylphenyl)ethane having a structure as represented by the following formula (10):

(10)

¹H-NMR (ppm, CDCl₃/TMS):

0.69–1.98 (36H), 4.29 (1H), 4.34–4.43 (1H), 4.65 (1H), 4.92 (1H), 5.22 (1H), 5.73 (1H), 6.70 (1H), 7.22–7.38 (4H)

MS (FAB, m/e): 486 [M+H]⁺

Element analysis (as C, H, N)

|  | C | H | N |
|---|---|---|---|
| Measured value (%) | 74.16 | 9.76 | 2.92 |
| Calculated value (%) | 74.19 | 9.75 | 2.88 |

EXAMPLE 8

Synthesis of 2-isopropyloxycarbonyloxy)-1-(4'-benzoyloxy-2',2',6',6'-tetramethyl-1'-piperidinyloxy)-1-(4'-vinylphenyl)ethane 2.76 g (10 mmol) of 4-benzoyloxy-2,2,6,6-tetramethylpiperidine-1-oxyl was dissolved into 15.0 g of 1,4-divinylbenzene and cooled down to 0° C.

After being added with 2.08 g (10 mmol) of di-isopropylperoxydicarbonate, the solution was heated for 5 hours at 55° C. in nitrogen gas flow.

The solution was then concentrated under reduced pressure and 3.16 g of objective substance was obtained by column chromatography (on silica gel; solution of dichloromethane/n-hexane (1/1) mixture as eluting solution), which corresponded to a yield of 62.1%. For identifying this substance, $^1$H-NMR analysis, MS analysis and element analysis were performed to have the results as given below. It was confirmed from these analytical results that the obtained substance was 2-(isopropyloxycarbonyloxy)-1-(4'-benzoyloxy-2',2',6',6'-tetramethyl-1'-piperidimyloxy)-1-(4'-vinylphenyl)ethane having a structure as represented by the following formula (11):

(11)

$^1$H-NMR (ppm, CDCl$_3$/TMS):

0.70–1.95 (22H), 4.28 (1H), 4.60 (1H), 4.75 (1H), 4.87 (1H), 5.15 (1H), 5.20 (1H), 5.71 (1H), 6.68 (1H), 7.25–7.95 (9H)

MS (FAB, m/e): 510[M+H]$^+$

Element analysis (as C, H, N)

|  | C | H | N |
|---|---|---|---|
| Measured value (%) | 70.75 | 7.70 | 2.72 |
| Calculated value (%) | 70.70 | 7.71 | 2.75 |

EXAMPLE 9

Synthesis of 2-(isopropyloxycarbonyloxy)-1-(4'-acetoxy-2',2',6',6'-tetramethyl-1'-piperidinyloxy)-1-(4'-vinylphenyl)ethane 2.14 g (10 mmol) of 4'-acetoxy-2,2,6,6-tetramethylpiperidine-1-oxyl was dissolved into 15.0 g of 1,4-divinylbenzene and cooled down to 0° C.

After being added with 2.08 g (10 mmol) of di-isopropylperoxydicarbonate, the solution was heated for 5 hours at 55° C. in nitrogen gas flow.

The solution was then concentrated under reduced pressure and 3.27 g of objective substance was obtained by column chromatography (on silica gel; solution of dichloromethane/n-hexane (1/1) mixture as eluting solution), which corresponded to a yield of 73.0%. For identifying this substance, $^1$H-NMR analysis, $^{13}$C-NMR analysis, MS analysis and element analysis were performed to have the results as given below. It was confirmed from these analytical results that the obtained substance was 2-(isopropyloxycarbonyloxy)-1-(4'-acetoxy-2',2',6',6'-tetramethyl-1'-piperidinyloxy)-(4'-vinylphenyl)ethane having a structure as represented by the following formula (12):

(12)

$^1$H-NMR (ppm, CDCl$_3$/TMS):

0.70–1.90 (22H), 2.00 (3H), 4.29 (1H), 4.64 (1H), 4.77 (1H), 4.88–5.04 (2H), 5.23 (1H), 5.74 (1H), 6.70 (1H), 7.25–7.40 (4H)

$^{13}$C-NMR (ppm, CDCl$_3$/TMS):

20.93, 21.19, 21.51, 21.54, 33.72, 33.93, 44.45, 44.56, 60.15, 60.47, 66.33, 68.56, 71.77, 83.70, 113.69, 125.86, 127.83, 136.37, 137.01, 139.21, 154.35, 170.44

MS (FAB, m/e): 448 [M+H]$^+$

Element analysis (as C, H, N)

|  | C | H | N |
|---|---|---|---|
| Measured value (%) | 67.06 | 8.35 | 3.13 |
| Calculated value (%) | 67.09 | 8.33 | 3.13 |

EXAMPLE 10

Synthesis of 2-(isopropyloxycarbonyloxy)-1-(di-t-butylnitroxyl)-1-(4'-vinylphenyl)ethane 1.44 g (10 mmol) of di-t-butylnitroxide was dissolved into 15.0 g of 1,4-divinylbenzene and cooled down to 0° C.

After being added with 2.08 g (10 mmol) of di-isopropylperoxydicarbonate, the solution was heated for 5 hours at 55° C. in nitrogen gas flow.

The solution was then concentrated under reduced pressure and 2.01 g of objective substance was obtained by column chromatography (on silica gel; solution of dichloromethane/n-hexane (1/1) mixture as eluting solution), which corresponded to a yield of 53.2%. For identifying this substance, $^1$H-NMR analysis, MS analysis and element analysis were performed to have the results as given below. It was confirmed from these analytical results that the obtained substance was 2-(isopropyloxycarbonyloxy)-1-(di-t-butylnitroxyl)-1-(4'-vinylphenyl)ethane having a structure as represented by the following formula (13):

(13)

¹H-NMR (ppm, CDCl₃/TMS):

1.13 (9H), 1.31–1.39 (15H), 4.33 (1H), 4.68 (1H), 4.77 (1H), 4.94 (1H), 5.24 (1H), 5.76 (1H), 6.71 (1H), 7.23–7.40 (4H)

MS (FAB, m/e): 378 [M+H]⁺

Element analysis (as C, H, N)

|  | C | H | N |
|---|---|---|---|
| Measured value (%) | 69.91 | 9.37 | 3.75 |
| Calculated value (%) | 69.99 | 9.34 | 3.71 |

EXAMPLE 11

Synthesis of a mixture of 2-(isopropyloxycarbonyloxy)-1-(4'-acetoxy-2',2',6',6'-tetramethyl-1'-piperidinyloxy)-1-(4'-vinylphenyl)ethane and 2-(isopropyloxycarbonyloxy)-1-(4'-acetoxy-2',2',6',6'-tetramethyl-1'-piperidinyloxy)-1-(3'-vinylphenyl)ethane By reaction in accordance with Example 9 except for the use of mixture of 1,3-divinylbenzene and 1,4-divinylbenzene (product of Nippon Steel Chemical Co., Ltd.; trade name: DVB-960) instead of 1,4-divinylbenzene, 3.16 g of objective substance was obtained, which corresponded to a yield of 70.5%.

Judging from the results of ¹H-NMR analysis, ¹³C-NMR analysis, LC-MS analysis and element analysis for identifying this substance, it was confirmed that the obtained substance was the mixture of 2-isopropyloxycarbonyloxy)-1-(4'-acetoxy-2',2',6',6'-tetramethyl-1'-piperidinyloxy)-1-(4'-vinylphenyl)ethane and 2-isopropyloxycarbonyloxy)-1-(4'-acetoxy-2',2',6',6'-tetramethyl-1'-piperidinyloxy)-1-(3'-vinylphenyl)ethane.

EXAMPLE 12

Synthesis of 2-(isopropyloxycarbonyloxy)-1-(4'-hydroxy-2',2',6',6'-tetramethyl-1'-piperidinyloxy)-1-(4'-vinylphenyl)ethane 1.72 g (10 mmol) of 4'-hydroxy-2,2,6,6-tetramethylpiperidine-1-oxyl was dissolved into 15.0 g of 1,4-divinylbenzene and cooled down to 0° C.

After being added with 2.08 g (10 mmol) of di-isopropylperoxydicarbonate, the solution was heated for 5 hours at 55° C. in nitrogen gas flow.

The solution was then concentrated under reduced pressure and 1.66 g of objective substance was obtained by column chromatography (on silica gel; solution of ethyl acetate/n-hexane (1/3) mixture as eluting solution), which corresponded to a yield of 41.0%. For identifying this substance, ¹H-NMR analysis, MS analysis and element analysis were performed to have the results as given below. It was confirmed from these analytical results that the obtained substance was 2-(isopropyloxycarbonyloxy)-1-(4'-hydroxy-2',2',6',6'-tetramethyl-1'-piperidinyloxy)-1-(4'-vinylphenyl)ethane having a structure as represented by the following formula (14):

(14)

¹H-NMR (ppm, CDCl₃/TMS):

0.70–1.85 (22H), 3.93 (1H), 4.29 (1H), 4.63 (1H), 4.77 (1H), 4.92 (1H), 5.23 (1H), 5.74 (1H), 6.70 (1H), 7.27–7.39 (4H)

¹³C-NMR (ppm, CDCl₃/TMS):

21.08, 21.54, 33.81, 34.01, 48.62, 60.20, 60.49, 62.86, 68.62, 71.78, 83.64, 113.66, 125.86, 127.83, 136.40, 136.98, 139.32, 154.37

MS (FAB, m/e): 406 [M+H]⁺

Element analysis (as C, H, N)

|  | C | H | N |
|---|---|---|---|
| Measured value (%) | 68.15 | 8.65 | 3.47 |
| Calculated value (%) | 68.12 | 8.70 | 3.45 |

EXAMPLE 13

Synthesis of a mixture of 2-(isopropyloxycarbonyloxy)-1-(4'-hydroxy-2',2',6',6'-tetramethyl-1'-piperidinyloxy)-1-(4'-vinylphenyl)ethane and 2-(isopropyloxycarbonyloxy)-1-(4'-hydroxy-2',2',6',6'-tetramethyl-1'-piperidinyloxy)-1-(3'-vinylphenyl)ethane By reaction in accordance with Example 12 except for the use of mixture of 1,3-divinylbenzene and 1,4-divinylbenzene (product of Nippon Steel Chemical Co., Ltd.; trade name: DVB-960) instead of 1,4-divinylbenzene, 1.64 g of objective substance was obtained, which corresponded to a yield of 40.5%.

Judging from the results of ¹H-NMR analysis, ¹³C-NMR analysis, LC-MS analysis and element analysis for identifying this substance, it was confirmed that the obtained substance was the mixture of 2-isopropyloxycarbonyloxy)-1-(4'-hydroxy-2',2',6',6'-tetramethyl-1'-piperidinyloxy)-1-(4'-vinylphenyl)ethane and 2-(isopropyloxycarbonyloxy)-1-(4'-hydroxy-2',2',6',6'-tetramethyl-1'-piperidinyloxy)-1-(3'-vinylphenyl)ethane in accordance with the following formula (15):

(15)

EXAMPLE 14

Synthesis of a mixture of 2-hydroxy-1-(4'-hydroxy-2',2',6',6'-tetramethyl-1'-piperidinyloxy)-1-(4'-vinylphenyl)ethane and 2-hydroxy-1-(4'-hydroxy-2',2',6',6'-tetramethyl-1'-piperidinyloxy)-1-(3'-vinylphenyl)ethane

2.24 g (5 mmol) of the mixture of 2-(isopropyloxycarbonyloxy)-1-(4'-acetoxy-2',2',6',6'-tetramethyl-1'-piperidinyloxy)-1-(4'-vinylphenyl)ethane and 2-(isopropyloxycarbonyloxy)-1-(4'-acetoxy-2',2',6',6'-tetramethyl-1'-piperidinyloxy)-1-(3'-vinylphenyl)ethane obtained in Example 11 was dissolved into 50.0 g of ethanol.

After being added with 8.0 g of 10% sodium hydroxide solution, the solution was refluxed for 2 hours. It was then concentrated under reduced pressure, added with 100 g of diethylether and washed three times with 50 g of water.

After being dried by sodium sulfate, the solution was concentrated and recrystalized from mixed solvent of ethyl acetate and n-hexane to obtain 1.13 g of objective substance, which corresponded to a yield of 71.0%.

For identifying this substance, ¹H-NMR analysis, MS analysis and element analysis were performed to have the results as given below. It was confirmed from these analytical results that the obtained substance was the mixture of 2-hydroxy-1-(4'-hydroxy-2',2',6',6'-tetramethyl-1'-piperidinyloxy)-1-(4'-vinylphenyl)ethane and 2-hydroxy-1-(4'-hydroxy-2',2',6',6'-tetramethyl-1'-piperidinyloxy)-1-(3'-vinylphenyl)ethane in accordance with the following formula (16):

(16)

¹H-NMR (ppm, CDCl₃/TMS):

1.15–2.00 (16H), 3.70–3.80 (1H), 3.90–4.05 (1H), 4.15–4.25 (1H), 5.20–5.30 (2H), 5.70–5.80 (1H), 6.60–6.80 (1H), 7.20–7.45 (4H)

MS (FAB, m/e): 320 [M+H]⁺

Element analysis (as C, H, N)

|  | C | H | N |
|---|---|---|---|
| Measured value (%) | 71.40 | 9.19 | 4.45 |
| Calculated value (%) | 71.44 | 9.15 | 4.38 |

EXAMPLE 15

Synthesis of a mixture of 2-hydroxy-1-(2',2',6',6'-tetramethyl-1'-piperidinyloxy)-1-(4'-vinylphenyl)ethane and 2-hydroxy-1-(2',2',6',6'-tetramethyl-1'-piperidinyloxy)-1-(3'-vinylphenyl)ethane 1.95 g (5 mmol) of the mixture of 2-(isopropyloxycarbonyloxy)-1-(2',2',6',6'-tetramethyl-1'-piperidinyloxy)-1-(4'-vinylphenyl)ethane and 2-(isopropyloxycarbonyloxy)-1-(2',2',6',6'-tetramethyl-1'-piperidinyloxy)-1-(3'-vinylphenyl)ethane obtained in Example 4 was dissolved into 50.0 g of ethanol.

After being added with 8.0 g of 10% sodium hydroxide solution, the solution was refluxed for 2 hours. It was then concentrated under reduced pressure, added with 100 g of diethylether and washed three times with 50 g of water.

After being dried by sodium sulfate, the solution was concentrated and 1.06 g of objective substance was obtained by column chromatography (on silica gel; solution of ethyl acetate/n-hexane (1/3) mixture as eluting solution), which corresponded to a yield of 70.0%. For identifying this substance, ¹H-NMR analysis, MS analysis and element analysis were performed to have the results as given below. It was confirmed from these analytical results that the obtained substance was the mixture of 2-hydroxy-1-(2',2', 6',6'-tetramethyl-1'-piperidinyloxy)-1-(4'-vinylphenyl)ethane and 2-hydroxy-1-(2',2',6',6'-tetramethyl-1'-piperidinyloxy)-1-(3'-vinylphenyl)ethane having a structure as represented by the following formula (17):

(17)

¹H-NMR (ppm, CDCl₃/TMS):

0.70–1.70 (17H), 3.72–3.82 (1H), 4.17–4.27 (1H), 5.20–5.30 (2H), 5.70–5.80 (1H), 6.60–6.80 (1H), 7.20–7.45 (4H)

MS (FAB, m/e): 304 [M+H]⁺

Element analysis (as C, H, N)

|  | C | H | N |
|---|---|---|---|
| Measured value (%) | 75.23 | 9.66 | 4.60 |
| Calculated value (%) | 75.21 | 9.63 | 4.62 |

In the next place, the high molecular radical polymerization initiator in accordance with this invention is described in detail. It is a high molecular compound having a molecular main chain from which an alkoxyamine group as represented by the said general formula (3) suspends.

In the general formula (3), $R^5$ represents a phenylene group optionally having a substituted group on the ring, $R^6$ represents a hydrogen, a tertiary alkyl group having 4–8 carbon atoms, a benzoyl group, a methylbenzoyl group or an $R^{13}OC(O)$ group, wherein $R^{13}$ represents a linear or branched alkyl group, an alkoxy alkyl group having 1–10 carbon atoms or a cycloalkyl group optionally having a substituted group on the ring. $R^7$ and $R^{12}$ are each linear or branched alkyl group having 1–10 carbon atoms or of cyclic structure where $R^7$ and $R^{10}$ are connected with each other having a total carbon number of 4–10, selected independently. In case of cyclic structure, they are optionally substituted either by an alkyl group, a hydroxy group, an acetoxyl group, a benzoyloxy group, a methoxy group or an oxo group.

The molecular weight of high molecular radical polymerization initiator according to this invention can be determined as desired depending on the required characteristics of graft polymer. Preferably, the molecular weight converted to that of styrene measurable by gel permeation chromatography (in the following called "GPC") should be between 3,000 and 500,000 in average, but more preferably between 5,000 and 400,000. If the molecular weight of high molecular radical polymerization initiator is lower than 3,000, produced graft polymer tends to exhibit the properties of its trunk polymer only insufficiently. With a molecular weight higher than 500,000, high molecular radical polymerization initiator tends to have a high viscosity in molten state or in the form of solution to lower the workability in the phase of production of the initiator and graft polymer.

In addition, the average number of suspending alkoxyamine groups per molecule of high molecular radical polymerization initiator according to this invention should preferably be between 3 and 200, but more preferably between 5 and 100. If the molecular weight of branch polymers of the graft polymer is increased sufficiently, even 1 or 2 alkoxyamine groups can be enough to exhibit the characteristics as graft polymer. However, an average number of alkoxyamine groups less than 3 is not desirable because high molecular compound having no alkoxyamine group within the molecule is apt to arise and the graft polymer thus produced tends to exhibit the properties of branch polymer only insufficiently. On the other hand, an average number more than 200 is also undesirable because the graft polymer thus produced tends to exhibit the properties of trunk polymer only insufficiently. The said high molecular radical polymerization initiator can be obtained in the following manner: A mixture comprising compound represented by the general formula (4) having a radical-polymerizing vinyl group and an alkoxyamine group within the same molecule (in the following called "compound A"), radical-polymerizing monomers (B1) and radical polymerization initiator (C) is to be heated in a temperature range where the radical polymerization initiator (C) decomposes, whereas the said compound (A) does not decompose (in the following called "first stage polymerization").

In the general formula (4), $R^5$ represents a phenylene group optionally having a substituted group on the ring, $R^6$ represents a hydrogen, a tertiary alkyl group having 4–8 carbon atoms, a benzoyl group, a methylbenzoyl group or an $R^{13}OC(O)$ group, wherein $R^{13}$ represents a linear or branched alkyl group or an alkoxy alkyl group having 1–10 carbon atoms or a cycloalkyl group optionally having a substituted group on the ring. $R^7$ and $R^{12}$ are each linear or branched alkyl group having 1–10 carbon atoms, or of cyclic structure where $R^7$ and $R^{10}$ are connected with each other having a total carbon number of 4–10, selected independently. In case of cyclic structure, they are optionally substituted either by an alkyl group, a hydroxy group, an acetoxyl group, a benzoyloxy group, a methoxy group or an oxo group. $R^{12}$ represents a hydrogen or a methyl group.

The following can be named as concrete examples of the compound (A) represented by the general formula (4): 2-(2',2',6',6'-tetramethyl-1'-piperidinyloxy)-2-(4'-vinylphenyl)ethanol, 2-(4'-hydroxy-2',2',6',6'-tetramethyl-1'-piperidinyloxy)-2-(3'-vinylphenyl)ethanol, 2-t-butoxy-1-(2',2',6',6'-tetramethyl-1'-piperidinyloxy)-1-(4'-vinylphenyl)ethane, 2-t-butoxy-1-(4'-hydroxy-2',2',6',6'-tetramethyl-1'-piperidinyloxy)-1-(3'-vinylphenyl)ethane, 2-t-butoxy-1-(4'-acetoxy-2',2',6',6'-tetramethyl-1'-piperidinyloxy)-1-(3'-vinylphenyl)ethane, 2-t-butoxy-1-(1'1'3'3'-tetramethyl-2'3'-dihydro-1'H-2-isoindolyloxy)-1-(4'isopropenylphenyl)ethane, 2-benzoyloxy-1-(2',2',6',6'-tetramethyl-1'-piperidinyloxy)-1-(4'-vinylphenyl)ethane, 2-(4'-methylbezoyloxy-1-(2',2',6',6'-tetramethyl-1'-piperidinyloxy)-1-(4'-vinylphenyl)ethane, 2-isopropyloxycarbonyloxy-1-(2',2',6',6'-tetramethyl-1'-piperidinyloxy)-1-(4'-vinylphenyl)ethane, 2-isopropyloxycarbonyloxy-1-(4'-hydroxy-2',2',6',6'-tetramethyl-1'-piperidinyloxy)-1-(3'-vinylphenyl)ethane, 2-(2'-ethoxyethyloxycarbonyloxy)-1-(4'-methoxy-2',2',6',6'-tetramethyl-1'-piperidinyloxy)-1-(4'-vinylphenyl)ethane, 2-cyclohexyloxycarbonyloxy-1-(4'-methyl-2',2',6',6'-tetramethyl-1'-piperidinyloxy)-1-(4'-vinylphenyl)ethane, 2-(2'-ethylhexyloxycarbonyloxy)-1-(2',2',6',6'-tetramethyl-1'-piperidinyloxy)-1-(4'-vinylphenyl)ethane, 2-(4'-t-butylcyclohexyloxycarbonyloxy)-1-(2',2',6',6'-tetramethyl-1'-piperidinyloxy)-1-(4'-vinylphenyl)ethane, 2-isopropyloxycarbonyloxy-1-(4'-benzoyloxy-2',2',6',6'-tetramethyl-1'-piperidinyloxy)-1-(4'-vinylphenyl)ethane, 2-isopropyloxycarbonyloxy-1-(2',2',6',6'-tetramethyl-1'-piperidinyloxy)-1-(4'-vinylphenyl)ethane, 2-isopropyloxycarbonyloxy-1-(di-t-butylnitroxyl)-1-(4'-vinylphenyl)ethane, etc. In this invention, radical-polymerizing monomers (B1) for the first stage polymerization can be chosen from those vinyl monomers which are capable of copolymerizing with compound (A) and suitable for composing trunk polymer of the objective graft polymer. The following can be named concretely as radical-polymerizing monomers (B1) capable of copolymerizing with compound (A): monomers of styrene system such as styrene, p-methylstyrene, chlormethylstyrene, α-methylstyrene, etc., vinyl monomers with a carboxyl group such as acrylic acid, methacrylic acid, crotonic acid, itaconic acid, maleic acid, fumaric acid, etc., vinyl monomers with an acid anhydride group such as maleic acid anhydride, itaconic acid anhydride, etc., vinyl monomers with an ester group such as methyl (meth)acrylate, ethyl (meth)acrylate, propyl (meth)acrylate, butyl (meth)acrylate, 2-ethylhexyl (meth)acrylate, decyl (meth)acrylate, 2-hydroxyethyl (meth)acrylate, 2-hydroxypropyl (meth) acrylate, 3 hydroxypropyl (meth)acrylate, hydroxybutyl (meth)acrylate, glycidyl (meth)acrylate, dimethyl fumarate, diethyl fumarate, dibutyl fumarate, etc., vinyl monomers with an isocyanate group such as 2-isocyanateethyl (meth) acrylate, m-isopropenyl-α,α-methylbenzyl isocyanate, etc., alkyl(meth)acrylate with a nitrogen such as N,N-dimethylaminoethyl (meth)acrylate, N,N-diethylaminoethyl (meth)acrylate, N-t-butylaminoethyl (meth)acrylate, etc., vinyl monomers with an amido group such as acrylamide, methacrylamide, N-methyl (meth)acrylamide, N-ethyl (meth)acrylamide, N,N-dimethyl (meth)acrylamide, N,N-dimethylaminopropyl (meth)acrylamide, etc., nitrogen vinyl monomers with an aromatic compound such as 2-vinylpyridine, 4-vinylpyridine, etc., vinyl monomers with a nitryl group such as acrylonitrile, methacrylonitrile, etc.

Most favorable radical-polymerizing monomers among the said monomers are those which contain a oxygen or nitrogen atom within their molecules or concretely as follows: vinyl monomers with a carboxyl group, vinyl monomers with an acid anhydride group, vinyl monomers with an ester group, vinyl monomers with an isocyanate group, alkyl(meth)acrylate with a nitrogen, vinyl monomers with an amido group, nitrogen vinyl monomers with an aromatic compound, vinyl monomers with a nitryl group, etc. These radical-polymerizing monomers can be used independently or in the form of a mixture of 2 or more types. As far as it is desirable to introduce different properties into trunk polymer from those of branch polymer in case of graft polymerization, only radical-polymerizing monomers other than those of styrene system may be used for the first stage polymerization. It is, however, more preferable to use a mixture containing 1 or more types of radical-polymerizing monomers other than those of styrene system. This is because the use of monomers including those of styrene system is more advantageous for controlling a molecular weight of branch polymer in higher accuracy when producing graft polymer by means of the high molecular radical polymerization initiator based on this invention.

Quantities of the said compound (A) and radical-polymerizing monomers (B1) used for the first stage polymerization according to this invention can be decided depending on the desired number of alkoxyamine groups per molecule of the high molecular radical polymerization initiator to be obtained. However, a molar ratio of (B1) to (A) should preferably be within a range of 10–500 times in usual cases. In case of a molar ratio of radical-polymerizing monomers (B1) under 10 times, the graft polymer obtained tends to exhibit the properties of trunk polymer insufficiently due to excessively small trunk polymer chain length between branch polymers. On the contrary, if the molar ratio being over 500 times, the properties of branch polymer cannot be exhibited sufficiently because of excessively large trunk polymer chain length between branch polymers.

The first stage polymerization according to this invention takes place by heating a mixture comprising the said compound (A), radical-polymerizing monomers (B1) and radical polymerization initiator (C) in a temperature range where the said radical polymerization initiator (C) decomposes, but the said compound (A) does not decompose.

To say concretely, the polymerization temperature should preferably be between 0° C. and 120° C., but more preferably between 20° C. and 100° C. A polymerization temperature under 0° C. makes a long time necessary until completion due to lower polymerization speed to be disadvantageous economically, while the said compound (A) decomposes remarkably in case of a temperature over 120° C. to make it difficult to control the graft polymer structure obtained finally to result in gel formation or a reduced graft polymer purity.

Usual organic peroxides or azo compounds can be used as the radical polymerization initiator (C) for the first stage polymerization based on this invention. Those which are capable of generating free radicals effectively under the said polymerization conditions, including temperature, are desirable and should be chosen as required in accordance with the polymerization temperature. The following are the concrete examples of radical polymerization initiator (C) used in normal cases: peroxyesters such as t-butyl peroxyneodecanoate, t-octyl peroxyneodecanoate, t-butyl peroxypivalate, t-hexyl peroxypivalate, t-butyl peroxy-2-ethylhexanoate, t-octyl peroxyisobutylate, t-butyl peroxyisopropylcarbonate, t-butyl peroxylaurate, t-butyl peroxybenzoate, etc., diacylperoxides such as isobutyryl peroxide, 3,3,5-trimethyl hexanoyl peroxide, lauroyl peroxide, benzoyl peroxide, etc., peroxydicarbonates such as dipropyl peroxydicarbonate, diisopropyl peroxydicarbonate, di(2-ethylhexyl) peroxydicarbonate, etc., peroxyketals, such as 1,1-bis(t-butylperoxy)-2-methyl cyclohexane, 1,1-bis(t-butylperoxy)-3,3,5-trimethyl cyclohexane, 1,1-bis(t-hexylperoxy)-3,3,5-trimethyl cyclohexane, 2,2-bis(4,4-di-t-butylperoxycyclohexyl), etc., azo compounds such as 2,2'-azobis(isobutyronitrile), 2,2'-azobis(2,4-dimethylvaleronitrile), 2,2'-azobis(cyclohexanenitrile), 2,2'-azobis(2-methylbutyronitrile), 2,2'-azobis(2,4-dimethyl-4-methoxyvaleronitrile), etc. It is also possible to start polymerization by generating free radicals through reduction of t-butylhydroperoxide, cumene hydroperoxide, etc. by means of reducing agents such as iron sulfide, copper sulfide, sodium ascorbate, etc. or through light irradiation to photopolymerization initiator. The first stage polymerization based on this invention can be performed by known methods such as bulk polymerization, suspension polymerization, solution polymerization, emulsion polymerization, etc. A suitable method can be chosen from them depending upon monomer type, polymerization temperature, the molecular weight of desired high molecular radical polymerization initiator, etc.

When suspension polymerization is employed for the first stage polymerization based on this invention, water-soluble, high molecular protective colloid agent or slightly soluble inorganic substance may be added as dispersion agent to polymerization system. Polyvinyl alcohol, polyvinyl pyrrolidone, methyl cellulose, etc. are available as water-soluble, high molecular protective colloid agent, among which polyvinyl alcohol is desirable. As slightly soluble inorganic substance, tricalcium phosphate, magnesium phosphate, calcium pyrophosphate, bentonite, etc. can be mentioned. If a slightly soluble inorganic substance is used as dispersion agent, it is desirable to add a small quantity of anion surface active agent such as sodium dodecyl benzene sulfonate, sodium α-olefin sulfonate, etc.

When solution polymerization is employed for the first stage polymerization based on this invention, the following solvents can be used individually or as a mixture: solvents of keton system such as toluene, xylene, ethylbenzene, etc., solvents of ester system such as ethyl acetate, butyl acetate, isobutyl acetate, etc., solvents of alcohol system such as methanol, isopropyl alcohol, n-butyl alcohol, etc., solvents of ethylene glycol system such as ethylene glycol, ethylene glycol diacetate, ethylene glycol monomethyl ether, ethylene glycol diethylether, ethylene glycol methyether acetate, etc., solvents of diethylene glycol system such as diethylene glycol, diethylene glycol dimethylether, diethylene glycol monobutylether, etc., solvents of propylene glycol system such as propylene glycol, propylene glycol methylether acetate, etc.

According to this invention, such known chain transfer agents as α-methyl styrene dimer (2,4-diphenyl-4-methyl-1-pentene), terpinolene, n-octyl mercaptan, t-dodecyl mercaptan, 2-mercapto ethanol, thiophenol, etc. can optionally be used.

After the first stage polymerization has completed, high molecular radical polymerization initiator according to this invention is supplied as it is or after being purified by solvent cleaning or reprecipitation, etc. to next polymerization process for obtaining graft polymer (in the following called "second stage polymerization").

The second stage polymerization according to this invention is performed by heating a mixture containing high molecular radical polymerization initiator represented by the said general formula (3) and radical-polymerizing monomers (B2).

Namely, high molecular radical polymerization initiator represented by the general formula (3) cracks thermally into carbon radical bound on trunk polymer side and stable nitroxide radical. Carbon radical begins addition polymerization with radical-polymerizing monomers (B2) in the system. On the other hand, nitroxide radical does not begin polymerization, but repeats re-bonding and re-cracking against growing polymer radical induced by carbon radical to proceed with the second stage polymerization in the form of radical polymerization similar to so-called living polymerization.

The second stage polymerization based on this invention can be performed, likely as in case of the first stage polymerization, by known methods such as bulk polymerization, suspension polymerization, solution polymerization, emulsion polymerization, etc. A suitable method can be chosen from them depending upon monomer type, polymerization temperature, the molecular weight of desired high molecular radical polymerization initiator, etc.

Suitable radical-polymerizing monomers (B2) for the second stage polymerization according to this invention can be chosen from those available for the first stage polymerization in dependence upon the properties required for graft polymer to be obtained. It is, however, preferable to use individual monomers of styrene system or a mixture comprising radical-polymerizing monomers containing at least one type of monomers of styrene system in order to effectively increase the molecular weight of branch polymer of graft polymer to be obtained by the second stage polymerization or to control it more accurately.

The molecular weight of branch polymer of graft polymer obtained by the second stage polymerization according to this invention can be determined as required on the basis of the relationship to the molecular weight of trunk polymer as well as in dependence upon the desired molecular weight of graft polymer. Although it may differs depending upon the number of alkoxyamine groups suspending in high molecular radical polymerization initiator (A) (namely the number of branch polymers to be obtained finally), the preferable molecular weight of branch polymer should usually be between 1,000 and 150,000, more preferably between 2,000 and 100,000, if converted to that of styrene measurable by GPC. If the molecular weight is under 3,000, graft polymer thus obtained tends to exhibit the properties of its branch polymer only insufficiently. If over 150,000, it tends to exhibit the properties of trunk polymer only insufficiently.

The polymerization temperature for the second stage polymerization according to this invention should preferably be between 100° C. and 180° C., more preferably between 110° C. and 160° C. Polymerization at a temperature under 100° C. takes longer time until completion due to slower decomposition of high molecular radical polymerization initiator. On the other hand, polymerization at a temperature over 180° C. makes it difficult to control polymerization speed and easily causes heat polymerization in which homopolymers of radical-polymerizing monomers (B2) added at the second stage polymerization are produced to lower the purity of graft polymer.

In the following, the high molecular polymerization initiator according to this invention is explained in detail on the basis of working examples. As far as the gist of this invention is not exceeded, the invention is not limited by the examples.

Incidentally, the compound (A) was synthesized in advance for obtaining the high molecular radical polymerization initiator according to the invention as follows:

<Synthesis of Compound (A)>

A mixture of 50 g of divinyl benzene (product of Nippon Steel Chemical Co., Ltd.; trade name: DVB-960; isomer mixture of m- and p-divinyl benzene; purity: 96%) and 8.61 g (50 mmol) of 4-hydroxy-2,2,6,6-tetramethylpiperidine-1-oxyl (HO-TEMPO) was put into a 100 ml 4-port flask equipped with agitator, condenser and nitrogen gas tube for the purpose of nitrogen substitution of the content. The content was then heated up to 50° C. and added with 11.6 g (55.6 mmol) of di-isopropylperoxydicarbonate (IPP) in parts within 20 minutes. After reaction for 5 hours at 50° C., the most part of divinyl benzene was removed under reduced pressure. The product thus obtained was purified by means of silica gel chromatography to obtain 12.8 g of cream-colored oily substance.

As a result of analyzing the structure by means of high-speed liquid chromatography (HPLC), mass analysis, $^1$H-NMR and $^{13}$C-NMR, it was confirmed that the product was a mixture of 2-isopropyloxycarbonyloxy-1-(4'-hydroxy-2',2',6',6'-tetramethyl-1'-piperidinyloxy)-1-(3'-vinylphenyl)ethane and 2-isopropyloxycarbonyloxy-1-(4'hydroxy-2'2'6'6'-tetramethyl-1'-piperidinyloxy)-1-(4'-vinylphenyl)ethane (in the following called "A-1"). Its purity amounted to 98% according to HPLC and GPC analysis.

The following compounds (called "A2"–"A4" respectively) for this invention were synthesized in the similar manner:

Mixture of 2-t-butoxy-1-(4'-hydroxy-2'2'6'6'-tetramethyl-1'-piperidinyloxy)-1-(3'-vinylphenyl)ethane and 2-t-butoxy-1-(4'-hydroxy-2'2'6'6'-tetramethyl-1'-piperidinyloxy)-1-(4'-vinylphenyl)ethane (purity: 98%, "A-2")

Mixture of 2-(4'-hydroxy-2'2'6'6'-tetramethyl-1'-piperidinyloxy)-2-(3'-vinylphenyl)ethanol and 2-(4'-hydroxy-2'2'6'6'-tetramethyl-1'-piperidinyloxy)-2-(4'-vinylphenyl)ethanol (purity: 99%, "A-3")

2-isopropyloxycarbonyloxy-1-(2'2'6'6'-tetramethyl-1'-piperidinyloxyl)-1-(4'-vinylphenyl)ethane (purity: 98%, "A-4")

EXAMPLE 16

Nitrogen was blown into the mixture of 0.62 g (1.5 mmol) of compound A-1 obtained in the above mentioned manner, 4.41 g (44.0 mmol) of methylmethacryrate, 0.010 g (0.049 mmol) of t-hexylperoxypivalate as polymerization initiator and 0.05 g of n-octylmercaptan as molecular weight adjusting agent, to remove oxygen. The contents were then poured into a 10 ml glass ampoule which was sealed for polymerization for 6 hours at a reaction temperature of 60° C. In the next place, the contents were dissolved into 50 ml of tetrahydrofuran (THF) and the solution was dripped onto 300 ml of methanol for reprecipitation of high molecular compound. After removing unreacted compound of A-1, MMA and HPV completely by repeating this purifying process, the product was allowed to stand for 24 hours at 30° C. under reduced pressure.

The weight of the high molecular compound obtained in the said process was 2.91 g, which corresponds to a yield of 58.2%. Through measurement of the molecular weight by

GPC, it was identified to be poly-MMA which has a number average molecular weight of 20,000 and a weight average molecular weight of 34,000, if converted to those of styrene.

Figure 1:
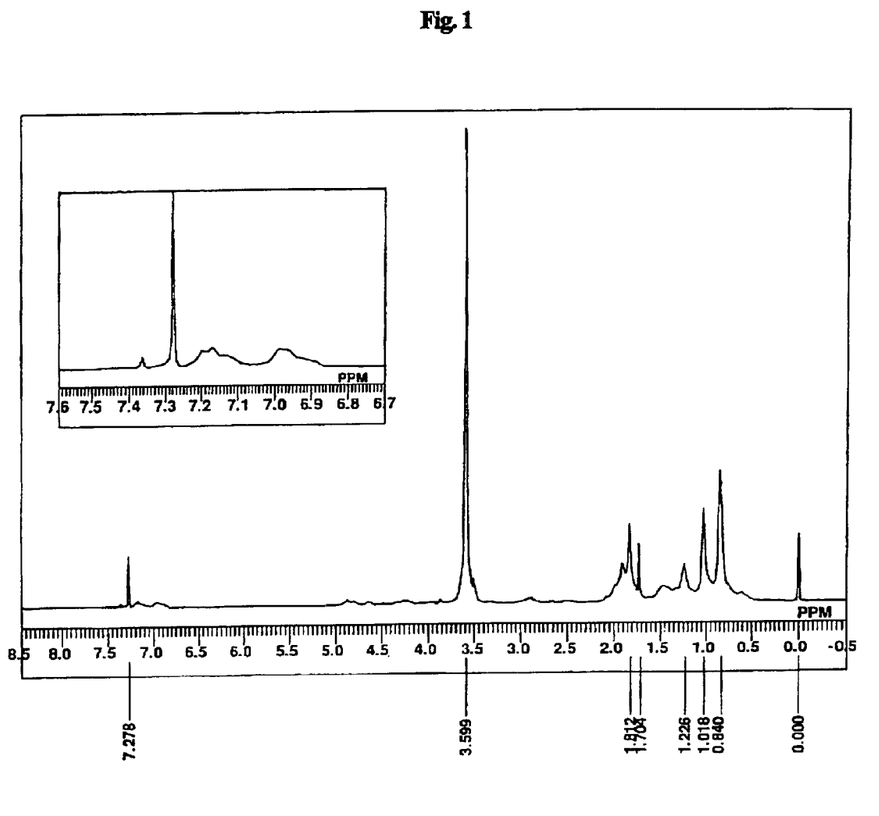
FIG. 1 shows $^1$H-NMR spectral diagram of a high molecular radical polymerization initiator in accordance with this invention, for example 16.

FIG. 1 shows the $^1$H-NMR spectrum of this compound (tetramethyl silane (TMS)/dichloroform (CDCl$_3$)). Assignment of each proton is as follows ($\delta$(ppm)):

| | |
|---|---|
| 0.65–1.55: | methyl and methylene proton |
| 1.65–2.15: | methyl proton |
| 3.60: | ester methyl proton |
| 6.8–7.3: | benzene ring proton |

Judging from the ratio between benzene ring proton derived from compound A-1 and proton derived from ester methyl groups of poly-MMA as a result of $^1$H-NMR analysis, introduction of 6.8 alkoxyamine groups per molecule of high molecular compound was ascertained.

Based on the above, the compound was confirmed to be the high molecular polymerization initiator according to this invention represented by the following formula (18) (in the following called "LRPI-1").

(18)

EXAMPLES 17–19

The high molecular polymerization initiators were synthesized in accordance with Example 16 except that the types and quantities of compound A and monomers as well as the polymerization temperature and duration were changed. The synthesizing conditions and the analytical results of the synthesized products are given in Table 1.

| Example | 17 | 18 | 19 |
|---|---|---|---|
| Compound (A) | 2 | 3 | 4 |
| | 0.57 g | 0.62 g | 0.49 g |
| | (1.5 mmol) | (1.5 mmol) | (1.5 mmol) |
| Monomer (B1) | MMA | MMA | CMS |
| | 4.41 g | 4.41 g | 5.2 g |
| | (44.0 mmol) | (44.0 mmol) | (34.1 mmol) |
| Polymerization initiator (C)* | HPV | BPV | BPV |
| | 0.11 g | 0.002 g | 0.023 g |
| | (0.54 mmol) | (0.011 mmol) | (0.13 mmol) |
| Additives | MSD | OM | — |
| | 0.044 g | 0.088 g | |
| Solvent | — | Toluene (4.4 g) | — |
| Polymerization temperature (° C.) | 60 | 60 | 70 |
| Polymerization duration (h) | 3 | 8 | 5 |
| Yield of high molecular compound (%) | 38 | 19 | 46 |

| Example | 17 | 18 | 19 |
|---|---|---|---|
| Number av. Molecular weight (unit: 1,000) | 107 | 9 | 47 |
| Weight av. Molecular weight (unit: 1,000) | 168 | 15 | 89 |
| Number of alkoxyamine groups per molecule of high molecular compound (pc) | 35.5 | 3.1 | 13.7 |
| $^1$H-NMR (TMS/CDCl$_3$) $\delta$ (ppm) | 0.6–1.6: CH$_3$, CH$_2$ 1.7–2.1: CH 3.60: CO$_2$CH$_3$ 6.8–7.3: phenyl | 0.6–1.6: CH$_3$, CH$_2$ 1.7–2.1: CH 3.60: CO$_2$CH$_3$ 6.8–7.3: phenyl | 0.6–1.2: CH$_3$ 1.3–2.1: CH, CH$_2$ 4.50: CH$_2$Cl 6.8–7.3: phenyl |
| Structural formula | Formula (19) | Formula (20) | Formula (21) |
| Abbreviation code | LRPI-2 | LRPI-3 | LRPI-4 |

*Quantity of polymerization initiator added: converted to that of quite pure initiator The abbreviations in the table above and in the following mean as follows, respectively:

Monomers

CMS: chloromethyl styrene (mixture of m-type and p-type)

Polymerization Initiator

HPV: t-hexyl peroxypivalate (product of Nippon Oil and Fats Co., Ltd.; trade name: Perhexyl PV)

BPV: t-butyl oxypivalate (product of Nippon Oil and Fats Co., Ltd.; trade name: Perbutyl PV)

Additives

MSD: α-methyl styrene dimer (product of Nippon Oil and Fats Co., Ltd.; trade name: Nofmer MSD)

OM: n-octyl mercaptan

(19)

(20)

(21)

(22)

EXAMPLE 20

30 g of diethyleneglycol dimethylether as solvent was put into a 300 ml 4-port flask equipped with agitator, condenser, thermometer and nitrogen gas tube. Vacant room in the solvent and the flask were fully substituted with nitrogen gas. The solvent was heated up to 65° C. While being agitated under nitrogen gas flow, mixture of 1.57 g (3.8 mmol) of compound A-1, 15.0 g (0.152 mol) of N,N-dimethylacrylamide (DMAA), 9.09 g of diethyleneglycol dimethylether and 0.167 g of BPV as polymerization initiator was added in 8 parts in intervals of 15 minutes. After being added, it was left at 65° C. for 3 hours and further at 85° C. for one hour for polymerization.

Gas chromatography and GPC analysis revealed that the DMAA inversion ratio amounted to 100% and that the solution contained high molecular compound by 30% (16.7 g). The number average molecular weight of the high molecular compound was 60,000, while the weight average molecular weight amounted to 134,000. The result of $^1$H-NMR (TMS/CDCl$_3$) analysis of high molecular compound taken out of a part of the solution is as shown below (in (ppm)):

| | |
|---|---|
| 0.6–1.6: | methyl and methylene proton |
| 1.7–2.2: | methyl proton |
| 3.0: | —N(CH$_3$)$_2$ |
| 6.8–7.3: | benzene ring proton |

Judging from the ratio between benzene ring proton derived from compound A-1 and proton derived from methyls bound to nitrogen atoms a result of $^1$H-NMR analysis, introduction of 15.5 alkoxyamine groups per molecule of high molecular compound was ascertained.

Based on the above, the compound was confirmed to be the high molecular polymerization initiator according to this invention represented by the following formula (22) (in the following called "LRPI-5").

EXAMPLE 21

2 g of LRPI-1 obtained according to Example 16 and 10 g of styrene were poured into a 20 ml glass ampoule, sealed after nitrogen substitution and left at 125° C. for 5 hours for polymerization. The contents were dissolved into 50 ml of THF and the solution was dripped onto 500 ml of methanol for reprecipitation of high molecular compound. After removing unreacted styrene monomers completely by repeating this purifying process, the high molecular compound was allowed to stand for 24 hours at 30° C. under reduced pressure.

The weight of the high molecular compound obtained was 7.0 g and the styrene inversion ratio amounted to 50.0%. According to GPC analysis, it showed a number average molecular weight of 66,000 and a weight average molecular weight of 97,000 if converted to those of styrene. In addition, as a result of fractional extraction by means of Soxhlet's extractor, it was confirmed that the high molecular compound obtained consists of 97% graft copolymer composed of styrene and MMA and 3% polystyrene homopolymer, and scarcely contains MMA homopolymer and gel. Furthermore, $^1$H-NMR analysis of graft polymer composition revealed that the branch polymer portion is composed of 68.5 styrene monomers in average.

EXAMPLES 22–25

By means of the high molecular radical polymerization initiators based on this invention synthesized according to Examples 17–20, the graft polymers based on this invention was synthesized in a similar manner as in Example 21 under the polymerizing conditions as shown in Table 2. The analytical results are also given in Table 2. BA in the table means butyl acrylate.

| Example | 22 | 23 | 24 | 25 |
|---|---|---|---|---|
| High molecular radical polymerization initiator | LRPI-2 2 g | LRPI-3 2 g | LRPI-4 2 g | LRPI-5 5 g |
| Monomer (B2) | Styrene 10 g | Styrene 10 g | Styrene 8 g BA 2 g | Styrene 5 g |
| Polymerization temperature | 125 | 125 | 125 | 125 |
| Polymerization duration | 3 | 1 | 2 | 5 |
| Inversion ratio of second stage monomer (B2) (%) | 35 | 19 | 27 | 54 |
| Number av. Molecular weight (unit: 1,000) | 294 | 17 | 95 | 104 |
| Weight av. molecular weight (unit: 1,000) | 388 | 25 | 175 | 196 |
| Graft polymer (%) | 98 | 98 | 98 | 97 |

-continued

| Example | 22 | 23 | 24 | 25 |
|---|---|---|---|---|
| Homopolymer of first Stage monomer (B1) (%) | 0 | 1 | 0 | 0 |
| Homopolymer of second stage monomer (2) (%) | 2 | 1 | 2 | 2 |
| Gel content (%) | 0 | 0 | 0 | 0 |
| Av. Number of monomer composing branch polymer of graft polymer | 50.4 | 25.5 | 33.1 | 20.0 |
| Number av. Molecular weight of branch polymer | 5,200 | 2,600 | 4,000 | 2,100 |

Industrial Applicability

As described above, the alkoxyamines containing a vinyl group as represented by the general formula (1) according to this invention are new compounds useful as radical generator, polymerization initiator for vinyl monomers, oxidation inhibitor for polymers of ethylene system, or scorch retarders at crosslinking polymers of ethylene system by heating. The said compounds show superior industrial applicability since they are stable against ionic reaction due to carbon-to-carbon bond between the vinyl group and the alkoxyamine group. Furthermore, the said compounds can be produced by the use of industrially available, cheap raw materials and in a simple production process comprises of a single step. By converting specific portions of the said compounds to an OH group, alkoxyamines containing a vinyl group and an OH group can be obtained, which are useful for introducing a functional group or for starting ring-opening polymerization.

In addition, those high molecular polymerization initiators can be obtained in a simple method according to this invention, from the molecular main chain of which alkoxyamine of special structure suspends by stable carbon-to-carbon bond. Besides, highly pure graft polymers whose trunk polymer and branch polymer are combined with each other by carbon-to-carbon bond to be stable against ionic reaction and radical reaction can be obtained by means of the high molecular radical polymerization initiators obtained as mentioned above.

Graft polymers obtainable by this invention have excellent effects as compatibilizer for mixing at least two different incompatible high molecular compounds uniformly, as surface active agent, as pigment dispersion agent, as adhesion improving agent, etc.

What is claimed is:

1. Alkoxyamines containing a vinyl group represented by the following general formula (1):

(1)

(In the formula, $R^1$ represents an aryl group or an $R^2O$ group, wherein $R^2$ represents a linear or branched alkyl group having 1–12 carbon atoms or a cycloalkyl group; $R^3$ and $R^4$ are each tertiary alkyl group having 4–6 carbon atoms or of cyclic structure where $R^3$ and $R^4$ are connected with each other having a total carbon number of 8–16. In case of cyclic structure, they are optionally substituted either by an alkyl group, an oxo group, a hydroxyl group, an acyloxy group or an alkoxy group).

2. Method for producing alkoxyamines containing a vinyl group represented by the following general formula (1), characterized in that a mixture comprising divinylbenzene, nitroxide compound and organic peroxide is heated up to the thermal decomposition temperature of the organic peroxide:

(1)

(In the formula, $R^1$ represents an aryl group or an $R^2O$ group, wherein $R^2$ represents a linear or branched alkyl group having 1–12 carbon atoms or a cycloalkyl group; $R^3$ and $R^4$ are each tertiary alkyl group having 4–6 carbon atoms or of cyclic structure where $R^3$ and $R^4$ are connected with each other having a total carbon number of 8–16. In case of cyclic structure, they are optionally substituted either by an alkyl group, an oxo group, a hydroxyl group, an acyloxy group or an alkoxy group).

3. Method for producing alkoxyamines containing a vinyl group described in claim 2, wherein the said organic peroxide is aromatic diacylperoxide or peroxydicarbonate.

4. Method for producing alkoxyamines containing a vinyl group represented by the following general formula (1), characterized in that organic peroxide is decomposed in a mixture comprising divinylbenzene, nitroxide compound and the said organic peroxide:

(1)

(In the formula, $R^1$ represents an aryl group or an $R^2O$ group, wherein $R^2$ represents a linear or branched alkyl group having 1–12 carbon atoms or a cycloalkyl group; $R^3$ and $R^4$ are each tertiary alkyl group having 4–6 carbon atoms or of cyclic structure where $R^3$ and $R^4$ are connected with each other having a total carbon number of 8–16. In case of cyclic structure, they are optionally substituted either by an alkyl group, an oxo group, a hydroxyl group, an acyloxy group or an alkoxy group).

5. Method for producing alkoxyamines containing a vinyl group described in claim 4, wherein the said organic peroxide is aromatic diacylperoxide or peroxydicarbonate.

* * * * *